United States Patent
Wu et al.

(10) Patent No.: US 10,178,975 B2
(45) Date of Patent: Jan. 15, 2019

(54) DETECTING SYSTEM AND MOBILE ELECTRONIC APPARATUS, AND METHOD FOR DETECTING PHYSIOLOGICAL CHARACTERISTIC THEREOF METHOD THEREOF

(71) Applicant: HTC Corporation, Taoyuan (TW)

(72) Inventors: Kuo-Chen Wu, Taoyuan (TW);
Meng-Hsi Wu, Taoyuan (TW);
Tung-Peng Wu, Taoyuan (TW)

(73) Assignee: HTC Corporation, Taoyuan (TW)

( * ) Notice: Subject to any disclaimer, the term of this patent is extended or adjusted under 35 U.S.C. 154(b) by 749 days.

(21) Appl. No.: 14/662,248

(22) Filed: Mar. 19, 2015

(65) Prior Publication Data

US 2016/0270739 A1   Sep. 22, 2016

(51) Int. Cl.
| A61B 5/00 | (2006.01) |
| A61B 5/0408 | (2006.01) |
| A61B 5/0295 | (2006.01) |
| A61B 5/026 | (2006.01) |
| A61B 5/024 | (2006.01) |

(52) U.S. Cl.
CPC ........ *A61B 5/7285* (2013.01); *A61B 5/02427* (2013.01); *A61B 5/04085* (2013.01); *A61B 5/0261* (2013.01); *A61B 5/0295* (2013.01); *A61B 5/6831* (2013.01); *A61B 5/721* (2013.01)

(58) Field of Classification Search
CPC .............. A61B 5/7285; A61B 5/02427; A61B 5/04085; A61B 5/721; A61B 5/6831; A61B 5/0261; A61B 5/0295
See application file for complete search history.

(56) References Cited

U.S. PATENT DOCUMENTS

| 4,295,472 A | 10/1981 | Adams |
| 4,331,154 A | 5/1982 | Broadwater et al. |
| 5,738,104 A | 4/1998 | Lo et al. |
| 7,171,259 B2 * | 1/2007 | Rytky ............... A61B 5/02438 600/509 |
| 7,379,770 B2 | 5/2008 | Szeto |

(Continued)

FOREIGN PATENT DOCUMENTS

| CN | 103876726 | 6/2014 |
| CN | 104257371 | 1/2015 |

OTHER PUBLICATIONS

Machine translation of CN 103876726.*

(Continued)

*Primary Examiner* — Mark Bockelman
(74) *Attorney, Agent, or Firm* — JCIPRNET

(57) ABSTRACT

A detecting system, a mobile electronic apparatus and a method for detecting a physiological characteristic thereof are provided. The mobile electronic apparatus includes a sensor unit, a PPG photoplethysmography (PPG) sensor, and a processing unit. The sensor unit has a first, second, and third sensing electrodes. The PPG sensor senses a PPG signal. The processing unit is coupled to the sensor unit and the PPG sensor. When the first and second sensing electrodes detect a voltage difference above a threshold, the PPG sensor is triggered to detect blood volume changes, and when the third sensing electrode is triggered to detect electrical activity of a heart between the first and third sensing electrodes, the PPG sensor is disabled by the processing unit.

16 Claims, 9 Drawing Sheets

(56) References Cited

U.S. PATENT DOCUMENTS

| | | |
|---|---|---|
| 7,697,982 B2 | 4/2010 | Brodnick |
| 8,086,301 B2 | 12/2011 | Cho et al. |
| 8,998,815 B2 * | 4/2015 | Venkatraman ......... A61B 5/721 |
| | | 600/481 |
| 2007/0016089 A1 | 1/2007 | Fischell et al. |
| 2010/0298657 A1 | 11/2010 | McCombie et al. |
| 2014/0257049 A1 | 9/2014 | Soundarapandian et al. |
| 2014/0275852 A1 | 9/2014 | Hong et al. |
| 2014/0275854 A1 | 9/2014 | Venkatraman et al. |
| 2014/0275888 A1 | 9/2014 | Wegerich et al. |
| 2014/0288391 A1 | 9/2014 | Hong et al. |

OTHER PUBLICATIONS

"Office Action of Taiwan Counterpart Application", dated Oct. 12, 2016, p. 1-p. 18.
"Office Action of Taiwan Counterpart Application", dated Jun. 1, 2017, p. 1-p. 5.
"Office Action of China Counterpart Application", dated Jun. 4, 2018, p. 1-p. 10.

* cited by examiner

DETECTING SYSTEM AND MOBILE ELECTRONIC APPARATUS, AND METHOD FOR DETECTING PHYSIOLOGICAL CHARACTERISTIC THEREOF METHOD THEREOF

BACKGROUND

Field of the Invention

The invention relates to a detecting system and a mobile electronic apparatus, and a method for detecting a physiological characteristic thereof. Particularly, the invention relates to the mobile electronic apparatus capable of removing noise of sensing signals to obtain information related to physiological characteristic.

Description of Related Art

In recent years, wearable electronic apparatuses are popular tools for human's life. The wearable electronic apparatuses can offer several functions. For example, the wearable electronic apparatuses can be used to detect the physiological characteristic of a detected object.

In conventional art, it has been proved that respiration signal can be extracted from an electrocardiogram (ECG) signal or a photoplethysmography (PPG) signal by a non-invasive way. However, for most cases, the existence of a motion artefact in the sensed signal from a detecting apparatus may reduce the accuracy of the obtained physiological characteristic. That is, to reduce the noise caused by the motion of the detected object is important in this art.

SUMMARY OF THE INVENTION

The invention is directed to a detecting system, and a mobile electronic apparatus thereof for detecting a physiological characteristic, and a method for detecting the physiological characteristic, which can obtain information related to the physiological characteristic efficiency and precisely.

The invention provides the mobile electronic apparatus including a sensor unit, a PPG photoplethysmography (PPG) sensor, and a processing unit. The sensor unit has a first, second, and third sensing electrodes. The PPG sensor senses a PPG signal. The processing unit is coupled to the sensor unit and the PPG sensor. When the first and second sensing electrodes detect a voltage difference above a threshold, the PPG sensor is triggered to detect blood volume changes, and when the third sensing electrode is triggered to detect electrical activity of a heart between the first and third sensing electrodes, the PPG sensor is disabled by the processing unit.

The invention provides a detecting system; the detecting system includes a mobile electronic apparatus and a wireless host. The mobile electronic apparatus includes a sensor unit, a PPG photoplethysmography (PPG) sensor, and a processing unit. The sensor unit has a first, second, and third sensing electrodes. The PPG sensor senses a PPG signal. The processing unit is coupled to the sensor unit and the PPG sensor. When the first and second sensing electrodes detect a voltage difference above a threshold, the PPG sensor is triggered to detect blood volume changes, and when the third sensing electrode is triggered to detect electrical activity of a heart between the first and third sensing electrodes, the PPG sensor is disabled by the processing unit. The wireless host is coupled to the mobile electronic apparatus, and the wireless host wirelessly receives information related to the physiological characteristic from the mobile electronic apparatus.

The invention also provides a method for detecting a physiological characteristic. The method includes: detecting a voltage difference over a first and second sensing electrodes of a sensor unit; triggering a PPG sensor to detect blood volume changes when the voltage difference is above a threshold; and disabling the PPG sensor when a third sensing electrode of the sensor unit is triggered to detect electrical activity of a heart between the first and third sensing electrodes.

According to the above descriptions, in the invention, the PPG sensor is used to detect the information related to the physiological characteristic of the detected object with the sensor unit. More particularly, whether the PPG sensor being enabled or not is determined by whether the third sensed signal is sensed or not. That is, the physiological characteristic detecting operation can be efficiently operated. Furthermore, by the PPG signal and the sensed signals, a noise provided by a motion of the detected object can be removed to obtain the physiological characteristic precisely.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

Figure 1:
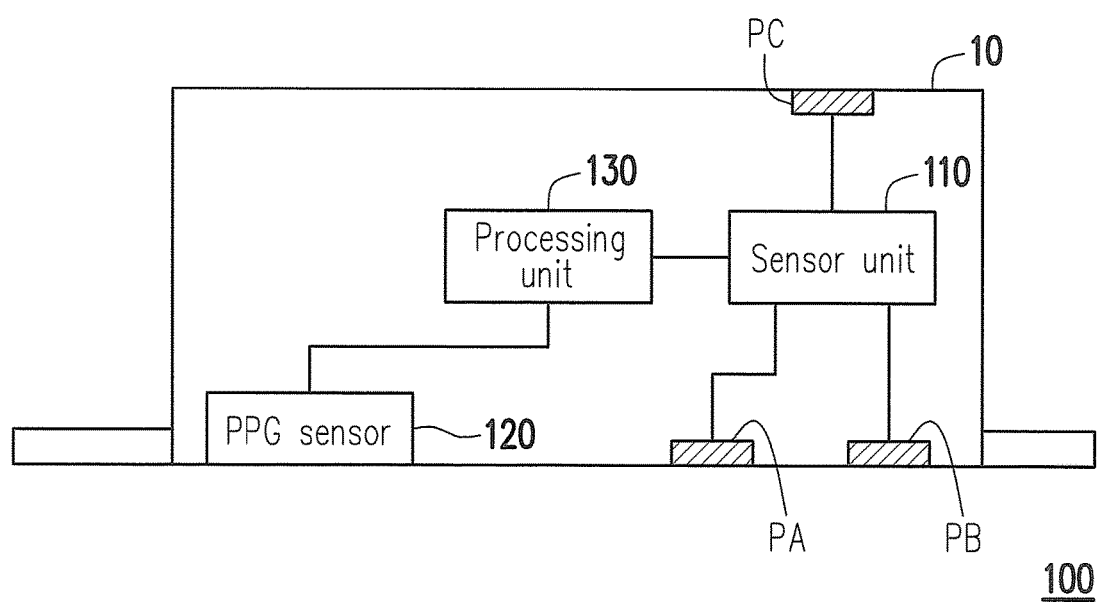
FIG. 1 illustrates a schematic diagram of an electronic apparatus according to an embodiment of the present disclosure.

Referring to FIG. 1, FIG. 1 illustrates a schematic diagram of an electronic apparatus according to an embodiment of the present disclosure. The electronic apparatus 100 includes a sensor unit 110, a photoplethysmography (PPG) sensor 120, and a processing unit 130. The sensor unit 110, the PPG sensor 120, and the processing unit 130 may be disposed in a main structure 10. The sensor unit 110 is coupled to the processing unit 130, and has a first electrode PA, second electrode TB, and third electrode PC. The sensor unit 110 may respectively receive a first, second, and third sensed signals by the first electrode PA, second electrode PB, and third electrode PC, and the sensor unit 110 may obtain a first, second, and third sensed signals based on the first, second, and third sensed signals, respectively. In this embodiment, the first electrode PA, second electrode PB are disposed on a same surface of the main structure 10, and the third electrode PC may be disposed on another surface of the main structure 10.

The PPG sensor 120 is coupled to the processing unit 130, and used to sense a PPG signal. In operation, the sensor unit 110 is enabled for sensing the first, second, and third sensed signals. The processing unit 130 may decide to enable the PPG sensor 120 according to a received status of the first and second sensed signals. In detail, when the first and second sensed signals can be sensed, and a voltage difference between the first and second sensed signals is above a threshold, the processing unit 130 may trigger the PPG sensor 120, and the PPG sensor 120 is triggered to detect blood volume changes.

On the other hand, after the PPG sensor 120 have been triggered, when the third sensing electrode PC is triggered to detect electrical activity of a heart between the first and third sensing electrodes, the PPG sensor 120 may be disable by the processing unit 130. Furthermore, the first, second, and third sensed signals are electrocardiogram (ECG) signals.

The processing unit 130 further obtains an information related to physiological characteristic according to the first, second sensed signals and one of the PPG signal and the third sensed signal. When the PPG sensor 120 is triggered, the third sensed signal is not available and the PPG signal is available. The processing unit 130 may process the first and second sensed signals and the PPG signal to obtain the information related to physiological characteristic. On the other hand, when the PPG sensor 120 is disabled, the third sensed signal is available and the PPG signal is not available. The processing unit 130 may process the first, second and third sensed signals to obtain the information related to physiological characteristic.

Please be noted here, each of the first, second and third sensed signals has a plurality of characteristic points. A voltage level of one characteristic point on the first sensed signal is different to a voltage level of corresponding characteristic point on the second sensed signal. The processing unit 130 may compare the voltage levels of the one characteristic point on the first sensed signal and the corresponding characteristic point on the second sensed signal to obtain a motion status of a detected object which is being detected.

Here, the first and second sensed signals may be obtained by coupling the first electrode PA and second electrode PB to a detected object. The first electrode PA and second electrode PB are respectively contact to a first position and second position on the detected object. There is a distance larger than 0 cm between the first position and second position.

The processing unit 130 further processes one of the third sensed signal and the PPG signal with the motion status, and a motion noise on the third sensed signal or the PPG signal may be remove. That is, information related to physiological characteristic of the detected object can be obtained precisely.

In additional, the information related to physiological characteristic may include information of heart beat, a pulse, and a respiration rate. The detected object may be an organism.

That is, when the detected object contacts the third electrode PC, and the third sensed signal can be sensed by the sensor unit 110, the processing unit 130 may process the third sensed signal with the motion status for removing the motion noise in the third sensed signal. The information of physiological characteristic of the detected object can be obtained precisely. On the other hand, when the detected object don't does not contact the third electrode PC, and the PPG signal can be sensed by the enabled PPG sensor 120, the processing unit 130 may process the PPG signal with the motion status for removing the motion noise in the PPG signal. The information related to physiological characteristic of the detected object also can be obtained precisely.

Referring to FIG. 2A-FIG. 2I, FIG. 2A-FIG. 2I illustrate waveform plots for processing the first and second sensed signal to obtain the motion status of the detected object according to an embodiment of present disclosure. The waveform in FIG. 2A may be the PPG signal obtained by the PPG sensor 120 or the third sensed signal obtained through the third electrode PC. The signal 210 may be used to be an input signal to the processing unit 130, and the processing unit 130 may decompose the signal 210 into multiple intrinsic mode function (IMF) modes IMF1-IMF5 through an Empirical Mode Decomposition (EMD) or Ensemble Empirical Mode Decomposition (EEMD) algorithm.

Of course, the decomposing operation using by the EMD/EEMD algorithm mentioned above is only an example, and the decomposing operation can be operated by any other decomposing algorithm in frequency domain.

Figure 2A:
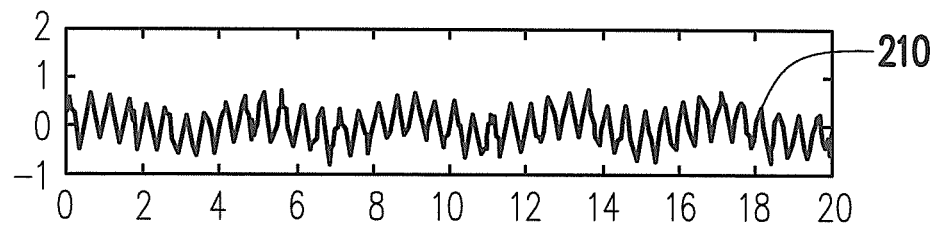
FIG. 2A-FIG. 2I illustrate waveform plots for processing the first and second sensed signal to obtain the motion status of the detected object according to an embodiment of present disclosure.
Figure 2B:
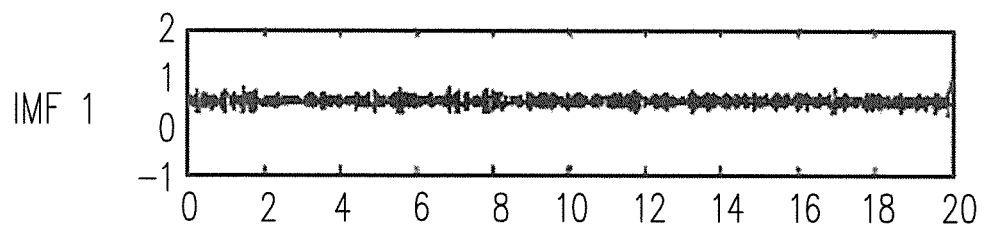
Figure 2C:
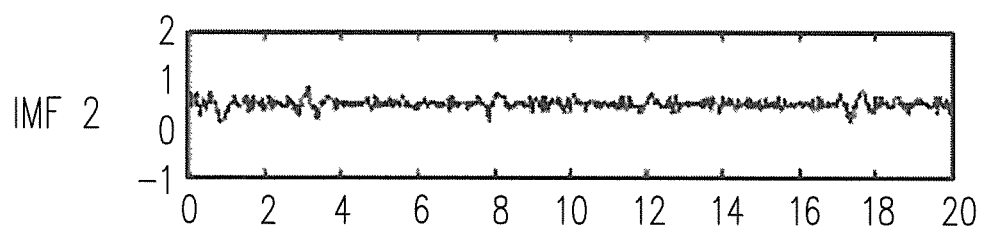
Figure 2D:
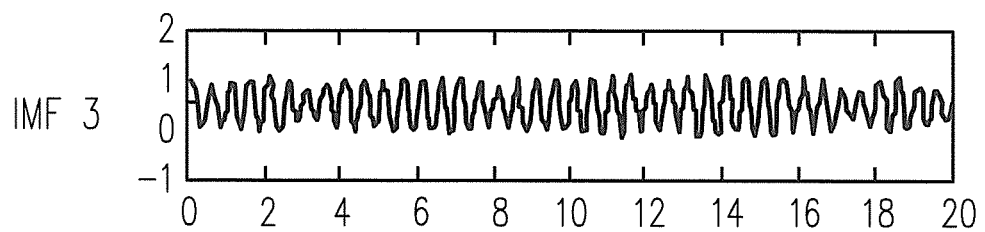
Figure 2E:
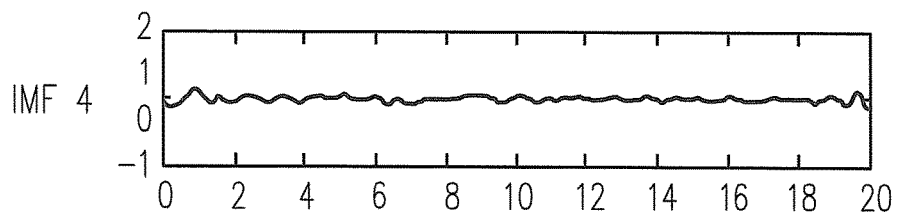
Figure 2F:
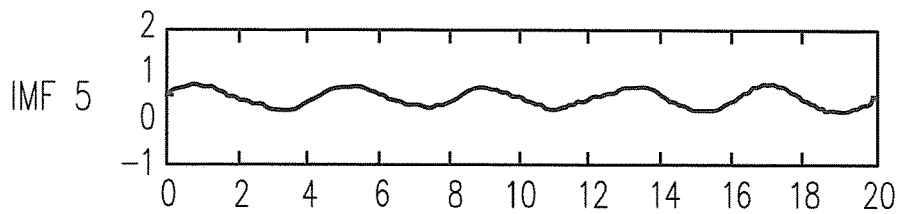
Figure 2G:
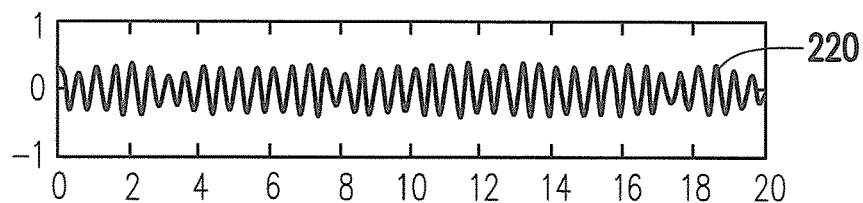
Figure 2H:
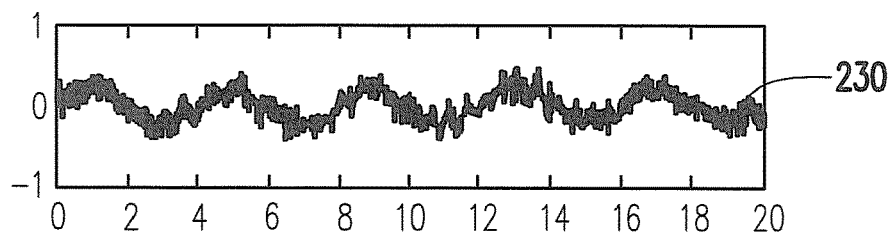
Figure 2I:
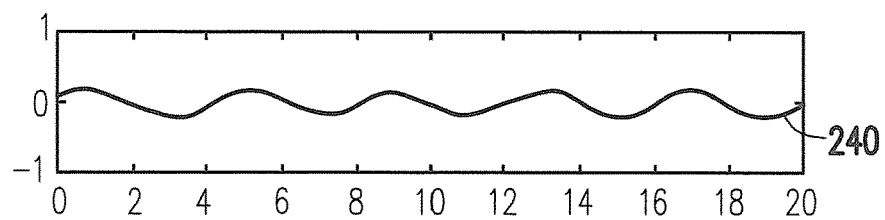

Referring to FIG. 2G, for example, the motion status of the detected object is detected, and a motion signal 220 is obtained according to the motion status. By comparing the motion signal 220 to the IMF modes IMF1-IMF5, the IMF mode IMF3 and the motion signal 220 are most alike. The IMF mode IMF3 may be defined to be the motion noise. Such as that, the processing unit 130 may remove the motion noise of the signal 210 to retrieve more accurate vital sign signal, and the signal 230 in FIG. 2H can be obtained. Furthermore, the processing unit 130 further processes the signal 230, and a respiratory signal 240 in FIG. 2I can be obtained. In this situation, the processing unit 230 may calculate the respiration rate according to the respiratory signal 240 more easily.

Figure 3:
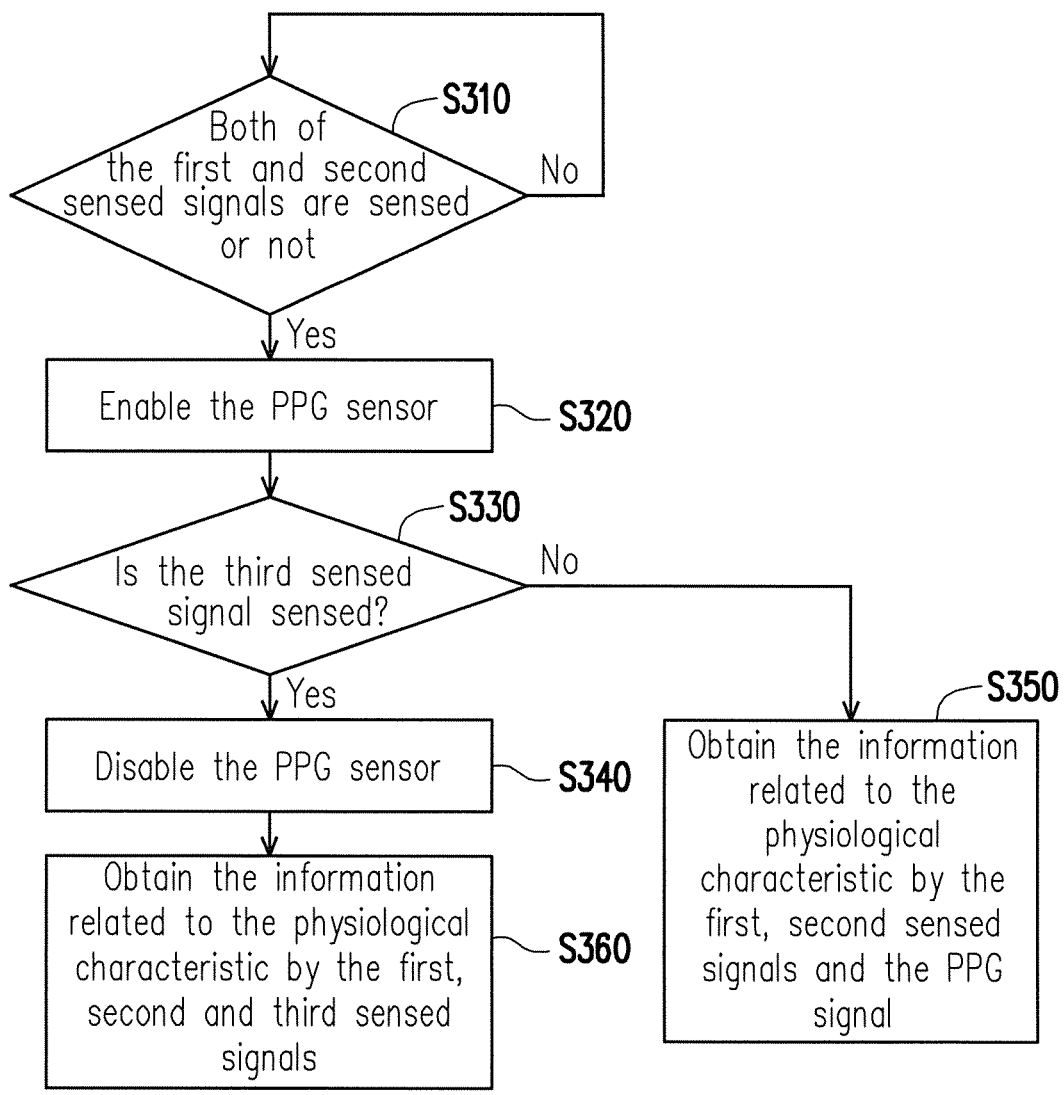
FIG. 3 illustrates a flow chart of a method for detecting a physiological characteristic.

Referring to FIG. 3, FIG. 3 illustrates a flow chart of a method for detecting a physiological characteristic. In the step S310, whether both of the first and second sensed signals are sensed or not is detected. The step S310 is used to detect both of the first and second electrodes are contacted by the detected objected or not. If both of the first and second electrodes are well contacted by the detected object, both of the first and second sensed signals can be sensed. In this case, when a voltage difference between the first and second sensing signals above a threshold, the step 320 can be executed, and the PPG sensor 120 can be enabled. Wherein, the threshold can be a pre-set value. On the contrary, if at least one of the first and second electrodes are not well contacted (or not contacted) by the detected object, both of the first and second sensed signals can't be sensed, the detecting operation of step S310 should be executed continuously.

Further, in the step S330, whether the third sensed signal are sensed or not is detected or not. That is, whether the third electrode PC of the sensor unit 110 being well contacted by the detected object or not is detected in the step S330. When the sensor unit 110 is well contacted by the detected object, the third sensing electrode is triggered to sense the third sensing signal, and when the sensor unit 110 is not well contacted (or not contacted) by the detected object, the third sensed signal cannot be sensed efficiently. If the third sensed signal is sensed, the step S340 can be executed, and if the third sensed signal is not sensed, the step S350 can be executed.

In the step S350, the processing unit 130 may obtain the information related to physiological characteristic by the first, second sensed signals and the PPG signal. Here, the processing unit 130 may use the first and second sensed signals to obtain the motion noise of the detected object, and the information related to physiological characteristic can be obtained according to the PPG signal by removing the motion noise.

In the step S340, the PPG sensor 120 is disabled. In the step S360, the processing unit 130 may obtain the information related to physiological characteristic by the first, second sensed signals and the third sensed signal. Here, the processing unit 130 may use the first and second sensed signals to obtain the motion noise caused by the detected object, and the physiological characteristic can be obtained according to the third sensed signal by removing the motion noise.

Figure 4:
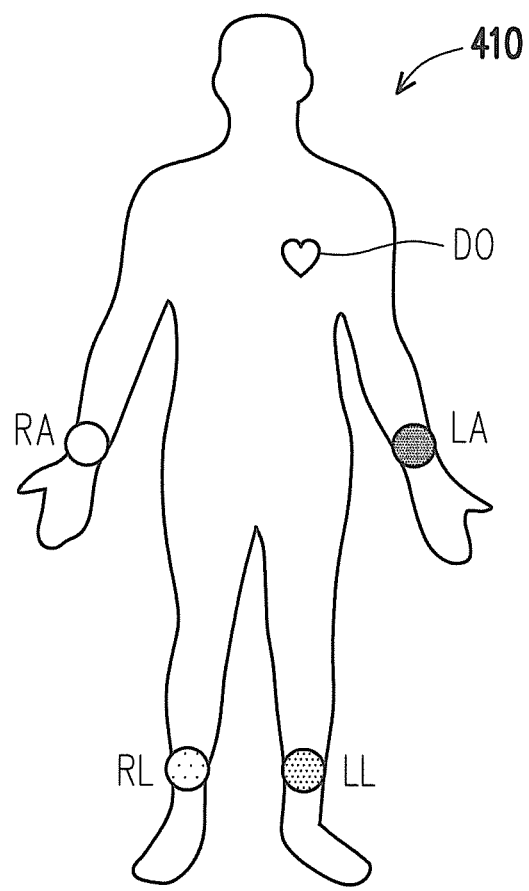
FIG. 4 illustrates a diagram for disposing the electrodes of the sensor unit on the detected object according to an embodiment of present disclosure.

Referring to FIG. 4 and FIG. 1, wherein FIG. 4 illustrates a diagram for disposing the electrodes of the sensor unit on the detected object according to an embodiment of present disclosure. In this embodiment, the detected object is a human 410. The first and the second electrodes PA and PB of the sensor unit 110 can be contacted to a same first limb of the human 410, and the third electrode PC of the sensor unit 110 can be contacted to a second limb, wherein, the first limb and the second limb are respectively on different sides of the human 410. For example, the first and the second electrodes PA and PB of the sensor unit 110 can be contacted to a right hand RA of the human 410, and the third electrode PC of the sensor unit 110 can be contacted to a left hand LA or a left leg LL of the human 410. Of course, the first and the second electrodes PA and PB of the sensor unit 110 can be contacted to the left hand LA of the human 410, and the third electrode PC of the sensor unit 110 can be contacted to the right hand RA or a right leg RL of the human 410.

It should be noted here, a first, second, and third positions respectively contacted by the first, second, and third electrodes PA, PB and PC of the sensor unit 110. In this embodiment, a detected object DO of the human 410 is disposed between each one of the first and second positions and the third position, wherein the detected object OB is a heart of the human 410.

Figure 5:
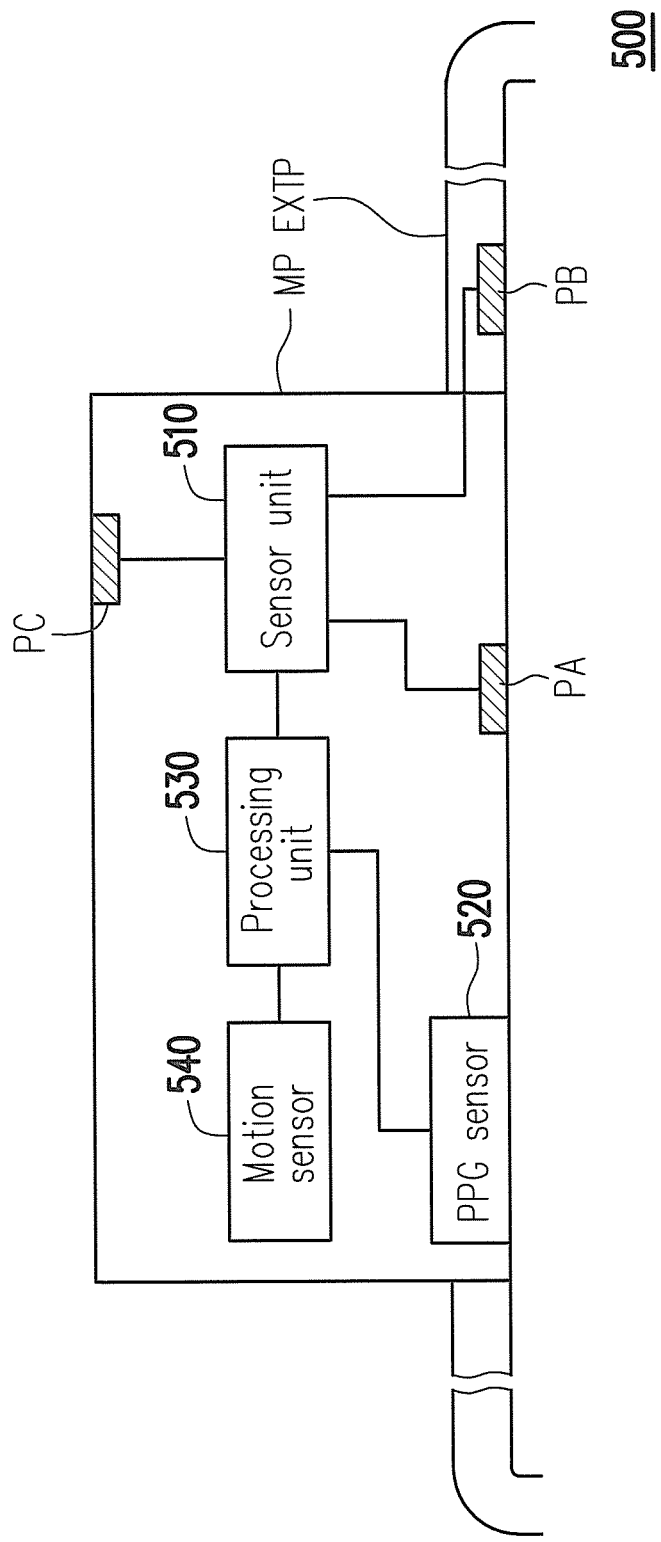
FIG. 5 illustrates a schematic diagram of an electronic apparatus according to the other embodiment of the present disclosure.

Referring to FIG. 5, FIG. 5 illustrates a schematic diagram of a mobile electronic apparatus according to the other embodiment of the present disclosure. The mobile electronic apparatus 500 includes a sensor unit 510, a PPG sensor 520, a processing unit 530, and a motion sensor 540. The mobile electronic apparatus 500 may be a watch. The sensor unit 510, PPG sensor 520, processing unit 530 and motion sensor 540 are disposed in an enclosure MP. Different from the embodiment in FIG. 1, the mobile electronic apparatus 500 further includes the motion sensor 540 for detecting the motion status of the mobile electronic apparatus 500. That is, the motion noise can be precisely detected, and the motion noise can be removed from the PPG signal or the sensed signal for obtaining the information related to physiological characteristic with high accuracy. In the embodiment, the motion sensor 540 may be a G-sensor or a Gyro sensor.

Figure 6:
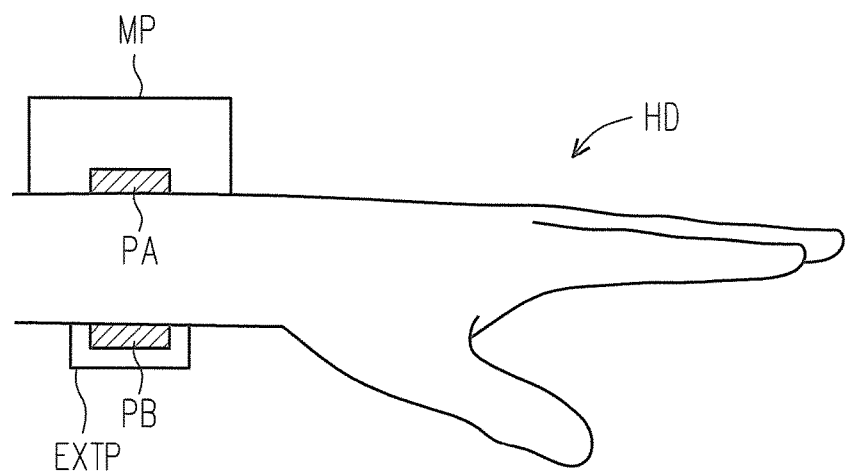
FIG. 6 illustrates a diagram for disposing the electrodes of the sensor unit on the detected object according to an embodiment of present disclosure.

On the other hand, the mobile electronic apparatus 500 further includes an flexible band EXTP. The first sensing electrode PA is disposed on a surface of the enclosure MP, and the second sensing electrode PB is disposed on a surface on the flexible band EXTP. Referring to FIG. 5 and FIG. 6, wherein FIG. 6 illustrates a diagram for disposing the sensing electrodes of the sensor unit on the detected object according to an embodiment of present disclosure. In FIG. 6, the mobile electronic apparatus 500 can be disposed on a hand HD of a detected human. The enclosure MP of the mobile electronic apparatus 500 can be put on a top surface of the hand HD, and the flexible band EXTP can be contacted to a bottom surface of the hand HD. That is, there is a distance between the positions on the hand HD contacted by the first sensing electrode PA and the second sensing electrode PB, and the distance may be extended. In FIG. 6, the second sensing electrode PB is facing toward the first sensing electrode PA.

The mobile electronic apparatus 500 may be an electronic watch or a smart band. For example, the mobile electronic apparatus 500 is the electronic watch, the enclosure MP may be body of the electronic watch, and the flexible band EXTP may be the strap of the mobile electronic apparatus 500. In FIG. 5, the second sensing electrode PB may be dispose on the surface of the strap of the mobile electronic apparatus 500.

Figure 7:
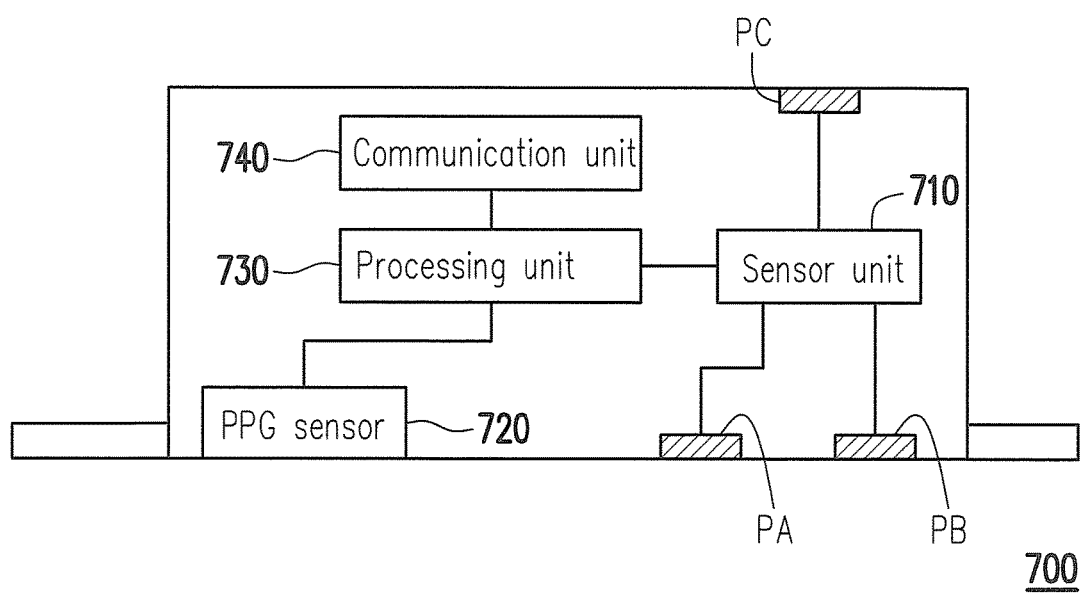
FIG. 7 illustrates a schematic diagram of an electronic apparatus according to another embodiment of the present disclosure.

Referring to FIG. 7, FIG. 7 illustrates a schematic diagram of a mobile electronic apparatus according to another embodiment of the present disclosure. The mobile electronic apparatus 700 includes a sensor unit 710, a PPG sensor 720, a processing unit 730, and a communication unit 740. Different from the embodiment in FIG. 1, the mobile electronic apparatus 700 further includes the communication unit 740. The communication unit 740 may be a wireless transmission unit, and is coupled to the processing unit 730. The communication unit 740 may wirelessly transmit information related to the physiological characteristic to an external wireless host. Of course, the communication unit 740 may also receive one or more signals from the external wireless host wirelessly. The communication unit 740 may be a blue-tooth unit, a near field communication (NFC) unit, a WIFI unit, or any other wireless transmission unit.

Figure 8:
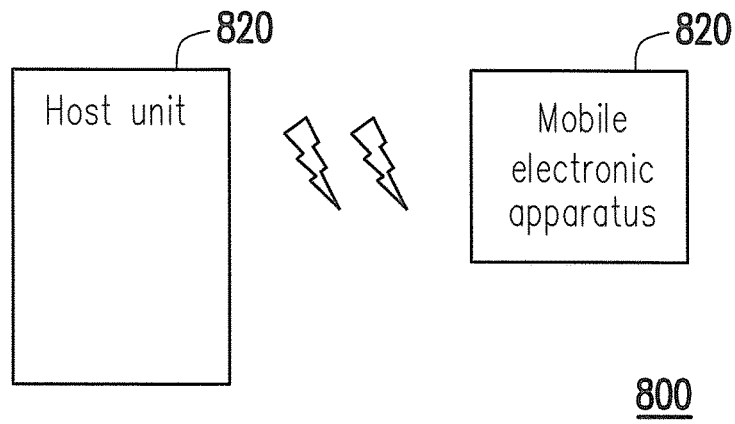
FIG. 8 illustrates a block diagram of a detecting system according to an embodiment of the present application.

Referring to FIG. 8, FIG. 8 illustrates a block diagram of a detecting system according to an embodiment of the present application. The detecting system 800 includes a mobile electronic apparatus 810 and a host unit 820. The host unit 820 may be a wireless host, and wireless coupled to the mobile electronic apparatus 810. The mobile electronic apparatus 810 may transport the information related to the physiological characteristic to the host unit 820. The host unit 820 may analysis the information related to the physiological characteristic for generating a detecting report. In the embodiment, the host unit 820 may be computer, smart phone, or any other electronic apparatus with a powerful processor and wireless communication ability.

Figure 9:
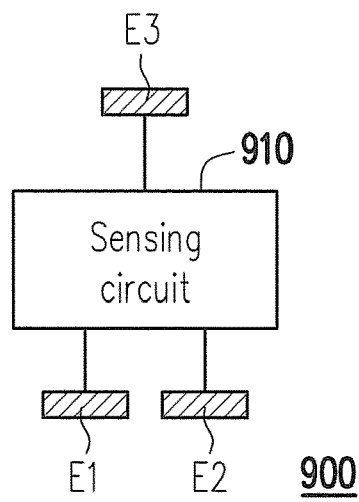
FIG. 9 illustrates a block diagram of the EGC sensor according to an embodiment of present disclosure.

Referring to FIG. 9, FIG. 9 illustrates a block diagram of the sensor unit according to an embodiment of present disclosure. The sensor unit 900 includes a sense processing unit 910, and electrodes E1-E3. The electrodes E1-E3 respectively forms a first, second, and third electrodes of the sensor unit 900, and the electrodes E1-E3 are coupled to the sense processing circuit 910. The electrodes E1-E3 respectively receive a first, second, and third sensed signals, and the sense processing circuit 910 generates a first, second, third sensed signals respectively according to the first, second, and third sensed signals. The sense processing circuit 910 may be used to process ECG signals.

Figure 10:
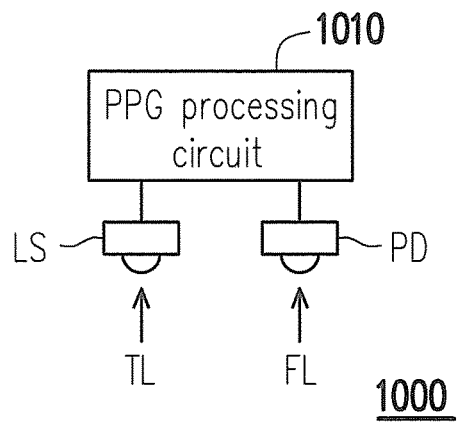
FIG. 10 illustrates a block diagram of the PPG sensor according to an embodiment of present disclosure.

Referring to FIG. 10, FIG. 10 illustrates a block diagram of the PPG sensor according to an embodiment of present disclosure. The PPG sensor 1000 includes a PPG processing circuit 1010, a light source LS, and a photodetector PD. The light source LS is coupled to the PPG processing circuit 1010, and transmitting a transmitting light TL according to a command from the PPG processing circuit 1010. The photodetector PD is coupled to the PPG processing circuit 1010, and receives a reflecting light FL which is generated according to the transmitting light TL, and response the reflecting light FL to the PPG processing circuit 101. Therefore, the PPG processing circuit can generate the PPG signal according to the reflecting light FL. Herein, the PPG signal may be related to an optically obtained plethysmograph, a volumetric measurement of an organ. The PPG signal may be obtained by using a pulse oximeter which illuminates the skin of the organ and measures changes in light absorption.

Figure 11:
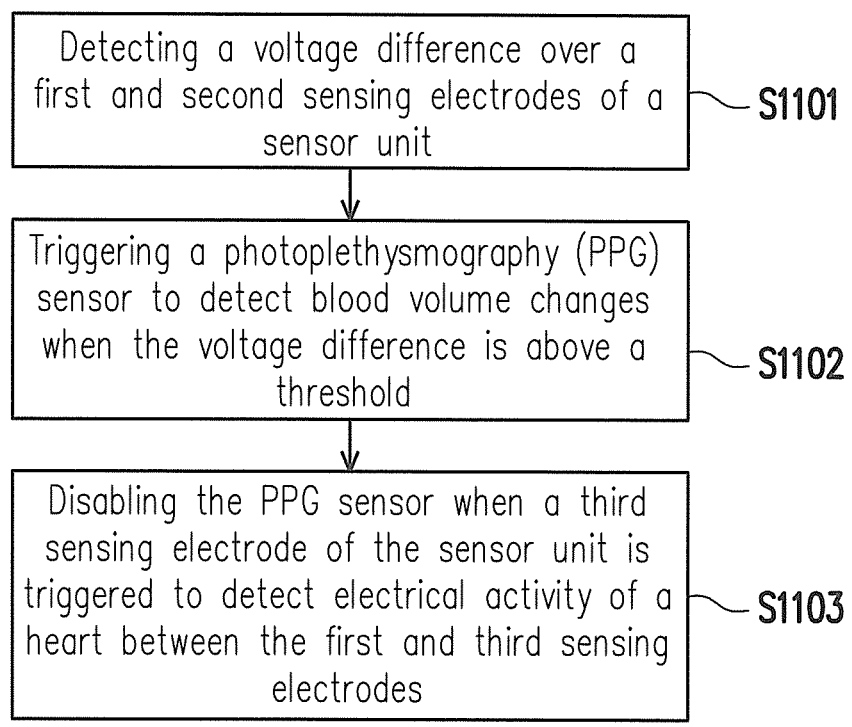
FIG. 11 illustrates a flow chart of a method for detecting a physiological characteristic according to an embodiment of present disclosure.

Referring to FIG. 11, FIG. 11 illustrates a flow chart of a method for detecting information related to a physiological characteristic according to an embodiment of present disclosure. In the step S1101, a voltage difference over a first and second sensing electrodes of a sensor unit is detected. In step S1102, a photoplethysmography (PPG) sensor is triggered to detect blood volume changes when the voltage difference is above a threshold. Further, in step S1103, when a third sensing electrode of the sensor unit is triggered to detect electrical activity of a heart between the first and third sensing electrodes, the PPG sensor is disabled.

The details of each of the steps in FIG. 11 have been disclosed in above embodiments, and no more repeated description here.

In summary, the present disclosure provides the sensor unit to generate the first and second sensed signal to obtain a motion status of the detected object. That is, a motion noise can be generated, and information related to a physiological characteristic can be obtained precisely by removing the motion noise from the PPG signal or the third sensed signal. The performance of the physiological characteristic detecting operation can be improved accordingly.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A mobile electronic apparatus, comprising:
   a sensor unit, having a first, second, and third sensing electrodes, the first, second and third sensing electrodes respectively receive a first, second and third sensed signal, each of the first sensed signal, the second sensed signal and the third sensed signal has a plurality of characteristic points;
   a photoplethysmography (PPG) sensor, sensing a PPG signal; and
   a processing unit, coupled to the sensor unit and the PPG sensor, and configured to compare voltage levels of one of the plurality of characteristic points on the first sensed signal and a corresponding characteristic points on the second sensed signal to obtain a motion signal,
   wherein when a voltage difference between a signal sensed by the first sensing electrode and a signal sensed by the second sensing electrodes is above a threshold, the PPG sensor is triggered to detect blood volume changes, when the processing unit triggers the third sensing electrode to detect electrical activity between the first and third sensing electrodes, the PPG sensor is disabled by the processing unit,
   wherein when the PPG sensor is not disabled by the processing unit, the processing unit decomposes the PPG signal into intrinsic mode function (IMF) modes and removes a mode signal that is most alike to the motion signal, when the PPG sensor is disabled by the processing unit, the processing unit decomposes the third sensed signal into IMF modes and removes the mode signal most alike to the motion signal.

2. The mobile electronic apparatus as claimed in claim 1, further comprising:
   an enclosure, wherein the sensor unit and the PPG sensor are disposed in the enclosure; and
   wherein, the first and second sensing electrodes are disposed on a first surface of the enclosure, and the third sensing electrode is disposed on a second surface of the enclosure and the first surface and second surface are not the same plane.

3. The mobile electronic apparatus as claimed in claim 1, further comprising:
   an enclosure, wherein the sensor unit and the PPG sensor are disposed in the enclosure; and
   an flexible band, contacts the enclosure at two sides,
   wherein, the first and third sensing electrodes are respectively disposed on a second and first surfaces of the enclosure, and the second electrode is disposed on the flexible band.

4. The mobile electronic apparatus as claimed in claim 3, wherein the second sensing electrode is facing toward the first sensing electrode.

5. The mobile electronic apparatus as claimed in claim 3, wherein the first and the second sensing electrodes facing toward the same direction and the third sensing electrode and first sensing electrode face toward different directions.

6. The mobile electronic apparatus as claimed in claim 1, wherein the sensor unit further comprises:
   a sensing circuit, coupled between the processing unit, and the first, second and third electrodes, the sensing circuit generating first, second, and third sensed signals according to signals detected from the first, second and third sensing electrodes.

7. The mobile electronic apparatus as claimed in claim 1, further comprising:
   a communication unit, coupled to the processing unit, for wirelessly transmitting information related to physiological characteristic to a wireless host.

8. A detecting system, comprising:
   a mobile electronic apparatus, comprises:
   a sensor unit, having a first, second, and third sensing electrodes, the first, second and third sensing electrodes respectively receive a first, second and third sensed signal, each of the first sensed signal, the second sensed signal and the third sensed signal has a plurality of characteristic points;
   a photoplethysmography (PPG) sensor, sensing a PPG signal; and
   a processing unit, coupled to the sensor unit and the PPG sensor, and configured to compare voltage levels of one of the plurality of characteristic points on the first sensed signal and a corresponding characteristic points on the second sensed signal to obtain a motion signal,
   wherein when a voltage difference between a signal sensed by the first sensing electrode and a signal sensed by the second sensing electrode is above a threshold, the PPG sensor is triggered to detect blood volume changes, when the processing unit triggers the third sensing electrode to detect electrical activity of a heart between the first and third sensing electrodes, the PPG sensor is disabled by the processing unit, wherein when the PPG sensor is not disabled by the processing unit, the processing unit decomposes the PPG signal into intrinsic mode function (IMF) modes and removes a mode signal that is most alike to the motion signal, when the PPG sensor is disabled by the processing unit, the processing unit decomposes the third sensed signal into IMF modes and removes the mode signal most alike to the motion signal; and a wireless host, coupled to the mobile electronic apparatus wirelessly to receive an information related to physiological characteristic from the mobile electronic apparatus.

9. The detecting system as claimed in claim 8, wherein the mobile electronic apparatus further comprising:
   an enclosure, wherein the sensor unit and the PPG sensor are disposed in the enclosure; and
   wherein, the first and second sensing electrodes are disposed on a first surface of the enclosure, and the third sensing electrode is disposed on a second surface of the enclosure and the first surface and second surface are not the same plane.

10. The detecting system as claimed in claim 8, wherein the mobile electronic apparatus further comprising:
    an enclosure, wherein the sensor unit and the PPG sensor are disposed in the enclosure; and
    an flexible band, contacts the enclosure at two sides,
    wherein, the first and second sensing electrodes are disposed on a first surface of the enclosure, and the third electrode is disposed on the flexible band.

11. The detecting system as claimed in claim 10, wherein the third sensing electrode is facing toward the first sensing electrode.

12. The detecting system as claimed in claim 10, wherein the first and the second sensing electrodes facing toward the same direction and the third sensing electrode and first sensing electrode face toward different directions.

13. The detecting system as claimed in claim 8, wherein the sensor unit further comprises:
    a sensing circuit, coupled between the processing unit, and the first, second and third electrodes, the sensing circuit generating first, second, and third sensed signals according to the signal detected from the first, second and third sensing electrodes.

14. The detecting system as claimed in claim 8, wherein the mobile electronic apparatus further comprises:
    a communication unit, coupled to the processing unit, for wirelessly transmitting information related to the physiological characteristic to the wireless host.

15. A method for detecting a physiological characteristic, comprising:
    detecting a voltage difference over a first and second sensing electrodes of a sensor unit, the first and second sensing electrodes respectively receive a first and second sensed signal, each of the first sensed signal and the second sensed signal has a plurality of characteristic points;
    comparing voltage levels of one of the plurality of characteristic points on the first sensed signal and a corresponding characteristic points on the second sensed signal to obtain a motion signal;
    triggering a photoplethysmography (PPG) sensor to detect blood volume changes when the voltage difference is above a threshold; and
    disabling the PPG sensor when a third sensing electrode of the sensor unit is triggered to detect electrical activity between the first and third sensing electrodes, wherein the electrical activity between the first and third sensing electrodes is a third sensed signal,
    wherein when the PPG sensor is not disabled, decompose the PPG signal into intrinsic mode function (IMF) modes and remove a mode signal that is most alike to the motion signal, when the PPG sensor is disabled, decompose the third sensed signal into IMF modes and remove the mode signal most alike to the motion signal.

16. The method as claimed in claim 15, further comprising:
    wirelessly transmitting information of physiological characteristic to a wireless host.

* * * * *